United States Patent [19]
Daddona et al.

[11] Patent Number: 4,946,668
[45] Date of Patent: Aug. 7, 1990

[54] TUMOR IMAGING WITH TECHNETIUM LABELLED GLUCARATE

[75] Inventors: Peter E. Daddona, West Chester; Koon Y. Pak, Bluebell; Mark Nedelman, Downingtown, all of Pa.

[73] Assignee: Centocor, Inc., Malvern, Pa.

[21] Appl. No.: 274,763

[22] Filed: Nov. 22, 1988

Related U.S. Application Data

[63] Continuation-in-part of Ser. No. 254,961, Aug. 7, 1988.

[51] Int. Cl.$^5$ .................. A61K 49/02; C07F 13/00
[52] U.S. Cl. .................................. 424/1.1; 534/14
[58] Field of Search .................. 424/1.1, 9; 534/14

[56] References Cited

U.S. PATENT DOCUMENTS

| | | | |
|---|---|---|---|
| 4,027,005 | 5/1977 | Adler et al. | 424/1.1 |
| 4,372,941 | 2/1983 | Ryan | 424/1.1 |
| 4,431,626 | 2/1984 | Henze | 424/1.1 |
| 4,666,698 | 5/1987 | Schwarz | 424/1.1 |
| 4,732,974 | 3/1988 | Nicolotti et al. | 424/1.1 X |

OTHER PUBLICATIONS

L. L. Hwang et al., *Int. J. App. Radiat. Isot.*, 36(6):475–480, (1985).
W. DeKieviet, *J. Nucl. Medicine*, 22:703–709 (1981).
C. D. Russell and A. G. Speiser, *J. of Nuclear Medicine*, 21(11):1086–1090 (1980).
W. H. Horner et al., *J. Nuclear of Medicine*, 21:525–528, (1980).
M. K. Dewanjee and H. W. Wahner, *Radiology* 132:711–716 (1979).
T. W. Ryerson et al., *Radiology*, 127:429–432 (1978).
A. J. Roberts et al., *Journal of Surgical Research*, 25:83–91 (1978).
D. R. Alonso et al., *The American Journal of Cardiology*, 42:251–258 (1978).
A. J. Roberts et al., *The Annals of Thoracic Surgery*, 27:42–48 (1978).
J. G. Jacobstein et al., *Journal of Nuclear Medicine*, 18(5):413–418 (1977).
Z. D. Grossman et al., *Journal of Nuclear Medicine*, 18(1):51–56 (1977).
B. L. Holman et al., *Radiology*, 121:427–430 (1976).
H. R. Schelbert et al., *Circulation Research*, 39(6):860–868 (1976).
N. Adler et al., *Journal of Nuclear Medicine*, 17(3):203–207 (1976).
D. J. Rossman et al., *Journal of Nuclear Medicine*, 16(11):980–985 (1975).
F. G. Zweiman et al., *Journal of Nuclear Medicine*, 16(11):975–979 (1975).
D. J. Rossmann et al., *Journal of Nuclear Medicine*, 16(11):875–878 (1975).
Y. Yonekura et al., *Journal of Nuclear Medicine*, 23(12):1133–1137 (1982).

*Primary Examiner*—John S. Maples
*Attorney, Agent, or Firm*—Hamilton, Brook, Smith & Reynolds

[57] ABSTRACT

Method using technetium-99m imaging agents for the study, detection or diagnosis of tumors. The imaging agents comprise a complex of technetium-99m and glucarate.

3 Claims, 2 Drawing Sheets

TUMOR IMAGING WITH TECHNETIUM LABELLED GLUCARATE

RELATED APPLICATIONS

This application is a continuation-in-part of U.S. Ser. No. 254,961 entitled "Technetium Imaging Agents" by Harvey J. Berger, Ban An Khaw, Koon Yan Pak and H. William Strauss filed Oct. 7, 1988.

BACKGROUND OF THE INVENTION

Radiolabeled compounds have long been used in diagnostic and therapeutic procedures. Some radio metals have superior properties for use in these procedures. Technetium-99m (Tc-99m) is an ideal radionuclide for scintigraphic imaging because of its radioactive decay properties. It has a single photon energy of 140 keV, a half life of about 6 hours, and it is readily available from a $^{99}$Mo-hu 99mTc generator.

There is a large family of polyhydric complexes of technetium, with and without carboxylic acid groups, which differ widely in stability. Hwang, et al., *Intl. J. of Appl. Radiat. Isot.*, 36 (6): 475-480 (1975). Hydroxycarboxylates tend to form soluble complexes with transition metals. Technetium (Tc) complexes of these compounds have been used for the nuclear imaging of kidneys, brain, myocardial infarcts and tumors. Russell and Speiser, *J. Nucl. Med.*, 21: 1086-1090 (1980). $^{99m}$Tc-D-glucoheptonate is the most widely used imaging agent. It has been used for brain and kidney imaging. Waxman, et al. *J.Nucl. Med.*, 17: 345-348 (1976) and Arnold, et al, *J. Nucl. Med.*,16: 357-367 (1975). See also, Adler, et al., U.S. Pat. No. 4,027,005. However, $^{99m}$Tc-D-glucoheptonate has been less successful as an imaging agent for myocardial infarct. Rossman, et al., *J. Nucl. Med.*,16: 980-985 (1975).

Much effort has been directed toward evaluating the usefulness of various radionuclides and radiopharmaceuticals for imaging tumor tissue, particularly malignant diseases such as breast carcinoma and colon carcinoma. $^{18}$F-2-fluoro-2-deoxy-D-glucose has been used to image cerebral gliomas, hepatoma, thyroid tumor, liver metastases from colon carcinoma and bone tumors. DiChiro et al., *Neurology*, 32:1323 (1982); Paul et al., *Lancet*, 1:50(1985); Joensuu et al., *Eur. J. Nucl. Med.*, 13:502 (1988); Yonekura et al., *Eur. J. Nucl. Med.*, 23:1133 (1982); Ahonen et al., *In: Nuclear Med., Proc. ENMC*, Stuttgart, N.Y., 441-443 (1986). However, this compound is not appropriate for all types of tumors. Accurate and early detection of tumors is often critical for the successful treatment of these diseases. Tumor imaging agents offer an effective, non-invasive method for early detection and imaging of tumors.

SUMMARY OF THE INVENTION

This invention pertains to a radionuclide imaging agent which is a complex of Tc-99m and a carbohydrate ligand, and a method for detecting tumors using the complex. The carbohydrate component is a compound having the general formula:

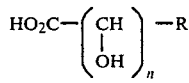

wherein n can be an integer from 1 to 10 inclusive; R can be -CO$_2$H, -PO$_3$H$_2$, -SO$_3$H, -N$^+$R'$_3$, -CHO, or an alkyl group having between one and five carbon atoms. The alkyl groups may be substituted, provided the substituents are not hydroxyl groups. R' can be a substituted or unsubstituted alkyl group having from 1 to 5 carbon atoms The carbohydrate component can be a salt, such as an alkali metal salt, of the carboxylate form of the compound.

The preferred complex is Tc-99m-glucarate. Tc-99m-glucarate is a biologically acceptable imaging agent for scintigraphic imaging of tumors including breast carcinoma, colon carcinoma and other tumors or malignancies in other organs and/or tissues.

In general, the method of detecting tumors using the Tc-99m-carbohydrate complex comprises: forming an aqueous mixture of Tc-99m in an oxidized form, such as the pertechnetate ion, with a reducing agent and the carbohydrate ligand of the formula above, such as glucaric acid, to provide a TC-99m-carbohydrate complex, administering the Tc-99m-carbohydrate complex to the subject, allowing the Tc-99m-carbohydrate to localize at the site of the tumor and scanning the subject with a gamma camera to obtain an image of the tumor.

The carbohydrate ligands employed in the method of this invention are capable of complexing technetium-99m in stable form without the formation of a significant amount of technetium colloids. For example, radiolabeled glucarate is stable in solution and, in addition, the labeling method can be performed rapidly (can be completed in less than one hour). The method can be performed at room temperature, at a pH between about 5-9. The labeled product does not require purification prior to administration.

DETAILED DESCRIPTION OF THE INVENTION

Figure 1A:
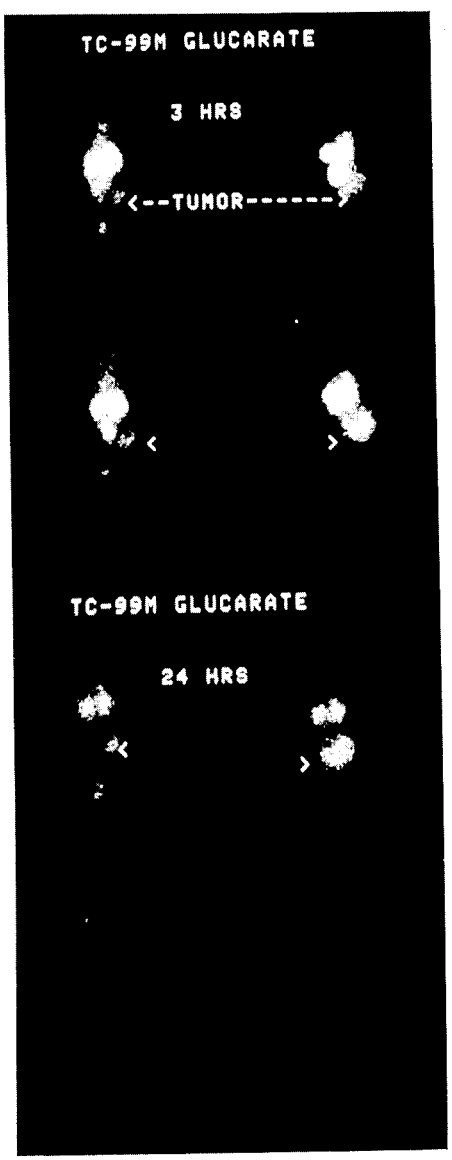
FIG. 1 shows scintigraphic images of color-ectal carcinoma in mice, taken at 3 and 5 hours (top) and 24 hours (bottom) after injection of (A) $^{99m}$Tc-glucarate and (B) TcO$_4$.

The Tc-99m-carbohydrate complex of this invention can be made by reacting Tc-99m in an oxidized state, with a carbohydrate ligand in the presence of a reducing agent, under conditions which allow formation of a stable complex between Tc-99m in a reduced state (e.g., IV or V valence state) and the carbohydrate ligand. The carbohydrate ligand is a compound having the general formula:

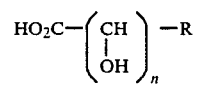

or salts thereof, wherein n can be an integer from 1 to 10 inclusive; and R can be -CO$_2$H, -PO$_3$H$_2$, -SO$_3$H, -N$^+$R'$_3$, -CHO, or a substituted or unsubstituted alkyl group having between one and five carbon atoms, provided that the substituents are not hydroxyl groups. R' can be an substituted or unsubstituted alkyl group having from 1 to 5 carbon atoms. The alkyl substituents can include amine groups or halogens, for example. The carbohydrate salts can be alkali metal salts (e.g., sodium or potassium). The ligand should be selected so that it complexes quickly with Tc-99m to form a stable, biologically acceptable complex.

Particularly preferred ligands are glucaric acid (also known as saccharic acid), or salts of glucaric acid, such as, for example, potassium glucarate. Glucaric acid complexes with Tc-99m quickly to form a stable Tc-99m-glucarate complex. Tc-99m labeled glucarate is a biologically acceptable imaging agent.

The source of Tc-99m should preferably be water soluble. Preferred sources are alkali and alkaline earth metal salts of pertechnetate ($TcO_4^-$) such as, for example, sodium pertechnetate. Tc-99m is most preferably obtained in the form of fresh sodium pertechnetate from a sterile Tc-99m generator (e.g., from a conventional $^{99}Mo/^{99m}Tc$ generator). Any other source of physiologically acceptable Tc-99m may be used.

Reducing agents must be physiologically acceptable and effective for reducing technetium-99m from its oxidized state to the IV or V oxidation state. Examples of suitable reducing agents are stannous chloride, stannous fluoride, stannous tartarate, and sodium dithionite. The preferred agents are stannous reducing agents, such as stannous chloride and stannous fluoride. The most preferred agent is stannous chloride.

The amount of reducing agent used is the amount necessary to reduce the technetium to provide for binding to the ligand in a reduced state. In a preferred mode, stannous chloride ($SnCl_2$) is the reducing agent, and the concentration may range from about 1 to about 1000 ug/ml, preferably from about 30 to about 500 ug/ml. The amount of the ligand may range from about 0.5 mg/ml up to the amount maximally soluble in the medium. In a preferred embodiment, where the ligand is glucarate, the amount of glucarate (as potassium glucarate) may range from about 0.5 mg/ml up to the amount maximally soluble in the medium. Preferred amounts of glucarate range from about 5 to about 30 mg/ml.

Tc-99m in the form of pertechnetate can be used in amounts up to about 50 mCi/ml, preferably from about 25 to about 50 mCi/ml.

The reaction between the pertechnetate ion and ligand is preferably carried out in aqueous solution at a pH at which the Tc-99m-carbohydrate complex is stable. Normally the pH for the reaction will be physiological pH, from about 5 to about 9, the preferred pH being from about 6 to about 8. The metal ion-ligand complex is incubated, preferably at a temperature from about 20° C. to about 60° C., most preferably from about 20° C. to about 37° C., for a sufficient amount of time for transfer of the metal ion to the ligand complex. Generally, less than one hour is sufficient to complete the reaction under these conditions.

In a preferred embodiment, aqueous sodium 99m pertechnetate is mixed with an aqueous solution of stannous reducing agent and glucaric acid (or salt thereof) to form Tc-99m-glucarate. The entire procedure can be conducted in less than one hour at room temperature and at a pH of from about 5 to about 9. Under these conditions, an essentially complete transfer of technetium-99m can be obtained. The various reagents used in the method, and the parameters of the method are discussed in detail below.

Tc-99m labeled carbohydrate can be used in scintigraphy for the imaging tumors. The Tc-99m-glucarate complex is particulary effective for imaging tumors such as breast carcinoma and colorectal carcinoma.

In the present method, an effective imaging amount of Tc-99m-carbohydrate preferably Tc-99m-glucarate, is injected parenterally (preferably intraveneously) into a subject. The dosage may vary, depending upon the area and tissue to be imaged, the age and condition of the patient and other factors which a skilled practitioner would consider. After injection, sufficient time is allowed for the Tc-99m-carbohydrate complex to accumulate at the site of the tumor. For example, Tc-99m-glucarate localizes to provide an image of breast carcinoma in mice within one hour of injection, with minimal liver and blood pool activity. A colorectal carcinoma image in mice was obtained within 3 hours of injection (FIG. 1). Thus, it is believed that Tc-99m-glucarate is diagnostically applicable within one to three hours of injection of the radiopharmaceutical in the subject. The subject can then be scanned with a gamma camera to detect the gamma emission of the Tc-99m, to thereby obtain an image of the tumor area. In this way, the tumor can be localized and its size can be determined.

The reagents for performing the labeling method can be assembled in kits for convenient performance of the method in the clinic. At minimum, a kit for radiolabeling the ligand with the radiometal can consist of a sealed and sterile vial containing reducing agent (preferably stannous ions) and the carbohydrate ligand (preferably glucaric acid) in aqueous solution. The pertechnetate ion is added to the vial containing the reducing agent and the ligand. The contents are then mixed and incubated for a time sufficient to effect labeling of the ligand. The radiolabeled ligand can then be used immediately without purification.

The invention is further illustrated by the following exemplification:

EXEMPLIFICATION

Example 1

Preparation of $^{99m}$Tc-Glucarate

Monopotassium glucarate (25 mg) was dissolved in 0.2M bicarbonate (1.0 ml) at pH 8.0. To 500 ul of glucarate solution, 40 ul of stannous chloride (2.5 mg/ml) in 0.1M acetic acid was added, followed by 500 ul of $^{99m}$Tc generator eluate (60 mCi). The resulting solution was allowed to stand for 5 minutes at room temperature, and then analyzed for radiochemical purity by paper chromatography (Whatman 3MM, 60% $CH_3CN$:40% $H_2O$)

Example 2

The Effect of Glucarate Concentration on the Formation of $^{99m}$TC-Glucarate $^{99m}$Tc-glucarate was prepared as described in Example 1 using different concentrations of potassium glucarate (0.09–12.25 mg/ml). The products were analyzed by paper chromatography (Whatman 3MM, 60% $CH_3CN$:40%$H_2O$; $^{99m}TcO_4$-Rf=1.0, $^{99m}$Tc-glucarate, Rf=0.4; $^{99m}TcO_2 \times H_2O$, Rf=0). The data in Table 1 show that a concentration of 6 mg/ml potassium glucarate in 0.2M bicarbonate is sufficient to completely stabilize the reduced technetium.

TABLE 1

Percent of $^{99m}TcO_2$ and $^{99m}$Tc-Glucarate After Incubation at Room Temperature for 1 Hr. at Various Concentrations of Glucaric Acid as Analyzed by Paper Chromatography.

TABLE 1

Percent of $^{99m}TcO_2$ and $^{99m}Tc$-Glucarate After Incubation at Room Temperature for 1 Hr. at Various Concentrations of Glucaric Acid as Analyzed by Paper Chromatography.

| Glucaric Acid (mg/ml) | % $^{99m}TcO2$ | % $^{99m}Tc$-Glucarate |
|---|---|---|
| 12.25 | .0 | 100.0 |
| 6.12 | .0 | 100.0 |
| 3.06 | 11.5 | 88.5 |
| 1.53 | 19.5 | 80.5 |
| 0.76 | 24.4 | 75.6 |
| 0.38 | 30.0 | 70.0 |
| 0.19 | 41.0 | 59.0 |
| 0.09 | 57.0 | 43.0 |

Example 3

Stability of $^{99m}Tc$-Glucarate

Samples of $^{99m}Tc$-glucarate prepared as described in Example 1 from 6 and 12 mg/ml potassium glucarate were analyzed over a period of 7 hours. The results shown in Table 2, indicate that the preparation made from 12 mg/ml glucarate was more stable, and was stable for a period of about 2 hours.

Table 2

Stability of $^{99m}Tc$-Glucarate at room temperature

TABLE 2

Stability of $^{99m}Tc$-Glucarate at room temperature

| Time Hours | 6.12 mg/ml | | 12.24 mg/ml | |
|---|---|---|---|---|
|  | % Tc-GLUC | % TcO4$^-$ | % Tc-GLUC | % TcO4$^-$ |
| 1 | 95 | 5 | 95 | 5 |
| 3 | 76 | 24 | 82 | 18 |
| 5 | 45 | 55 | 62 | 38 |
| 7 | 36 | 64 | 60 | 40 |

Example 4

Biodistributiion of $^{99m}Tc$-Glucarate in Various Organs in Balb/c Mice

Biodistribution studies were carried out in Balb/c mice. The mice (3 mice per group) were injected intravenously with 100 uCi of technetium-labeled D-glucarate. Groups of mice were sacrificed 1, 4 and 8 hours after injection, and the organs removed, weighed and counted.

Table 3 shows the uptake of Tc-99m-glucarate by various organs at times ranging from 1-24 hours.

Table 3

Biodistribution In % Injected Dose Per Gram of $^{99m}$Technetium Labeled D-Glucarate At 1, 4, 8 and 24 Hours Post Injection In Mice

TABLE 3

Biodistribution In % Injected Dose Per Gram Of Technetium Labeled D-Glucarate At 1, 4, 8 and 24 Hours Post Injection In Mice

|  | 1 Hour | 4 Hours | 8 Hours | 24 Hours |
|---|---|---|---|---|
| Blood | 1.72 ± 0.43 | 1.26 ± 0.22 | 0.90 ± 0.29 | 0.56 ± 0.09 |
| Spleen | 0.44 ± 0.76 | N/A | N/A | N/A |
| Stomach | 0.935 ± 0.54 | 3.49 ± 5.10 | 1.13 ± 0.98 | 0.39 ± 0.34 |
| Intestine | 2.90 ± 1.12 | 2.02 ± 0.90 | 0.89 ± 0.46 | 0.58 ± 0.36 |
| Kidneys | 24.3 ± 4.15 | 28.50 ± 0.75 | 19.20 ± 5.00 | 8.4 ± 1.74 |
| Liver | 1.54 ± 0.51 | 1.49 ± 0.08 | 1.03 ± 0.18 | 0.42 ± 0.05 |
| Lungs | 3.90 ± 1.80 | 3.43 ± 1.35 | 1.95 ± 1.04 | 1.52 ± 1.02 |
| Heart | 0.63 ± 1.10 | 0.75 ± 1.30 | 0.30 ± 0.52 | N/A |
| Muscle | 0.32 ± 0.20 | 2.31 ± 2.98 | 0.59 ± 0.82 | 0.68 ± 1.00 |

TABLE 3-continued: Biodistribution In % Injected Dose Per Gram Of Technetium Labeled D-Glucarate At 1, 4, 8 and 24 Hours Post Injection In Mice N/A = Not Available N/A=Not Available

Example 5

Detection Of Colorectal Carcinoma In Mouse

Colorectal carcinoma was produced in female athymic nude mice by injecting subcutaneously $1 \times 10^7$ HT-29 cells (M.D. Anderson Hospital and Tumor Institute Houston, Tex.) per mouse in the hind limb. After 4 weeks, tumor bearing mice (2 per group) were injected intravenously with either sodium per-technetate (TcO4$^-$) or Tc-99m-glucarate (approximately 350 uCi/mouse). These mice were serially imaged with a gamma scintillation camera equipped with a pinhole collimator at 3, 5 and 24 hours. After imaging at the last time point, animals were killed, tumors and organs were weighed and quantitated for the distribution of radioactivity.

Figure 1B:
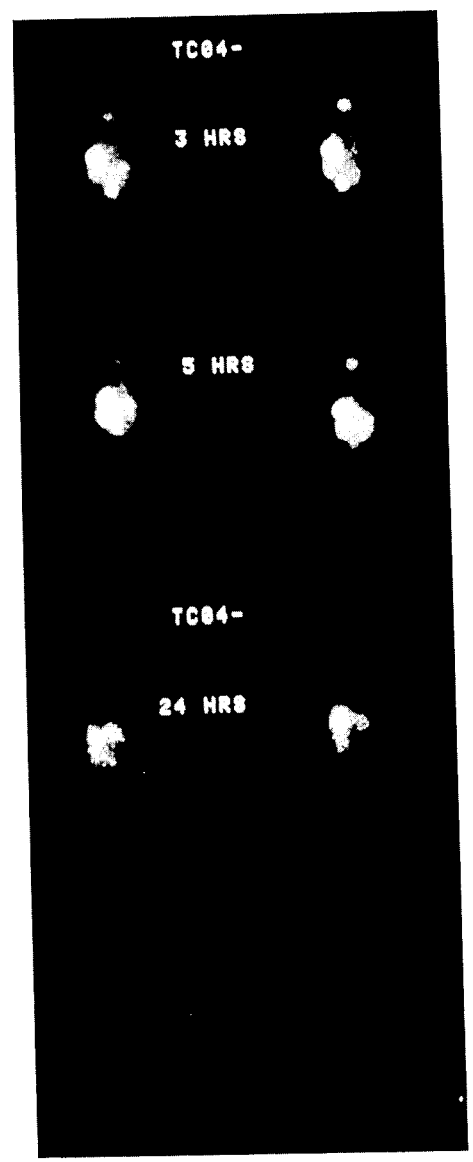

Scintigraphic images taken at 3, 5 and 24 hours after the injection of Tc-99m-glucarate showed uptake at the tumor site. The sizes of the tumor were 0.92 and 3.6 gm for the mouse shown on left and right, respectively. (FIG. 1A). The group that was injected with TcO4$^-$ displayed nonspecific uptake of radioactivity at the thyroid and stomach, and no tumor visualization was detected. (FIG. 1B). The sizes of the tumor for these two mice were 0.79 and 1.2 for the mouse shown on the left and right, respectively in FIG. 1.

Table 4 summarizes the uptake of radioactivity between Tc-99m-glucarate and TcO4$^-$ at 22 hours. The Tc-99m-glucarate showed three times more of the percent injected dose per gram (% ID/gm) of radioactivity at the tumor site in comparison to the nonspecific control TcO4$^-$.

Table 4

Uptake of Radioactivity Between Tc-99m Glucarate and TcO4$^-$ at 22 hours

TABLE 4

Uptake of Radioactivity Between Tc-99m Glucarate and TcO$^-_4$ at 22 hours

| %ID/gm | Tc-99m Glucarate | TcO$^-_4$ |
|---|---|---|
| at tumor site | 0.925 ± 0.04 | 0.29 ± 0.00 |
| tumor/blood | 2.79 ± 0.17 | 2.08 ± 0.21 |
| tumor/muscle | 14.30 ± 1.31 | 12.08 ± 3.41 |

Example 6

Detection Of Breast Tumor In Mice

Breast carcinoma was generated by injected female athymic nude mice with $1 \times 10^7$ BT-20 cells per mouse subcutaneously in the shoulder region. After 2 weeks, the tumor bearing mice (n=2) were injected with 300 uCi of Tc-99m-glucarate, and serially imaged with a gamma scintillation camera equipped with a pinhole collimator at 1, 3, 5 and 22 hours. After imaging at the last time point, animals were killed and necropsied. Organs were weighed and their activities were measured in a gamma counter.

Figure 2:
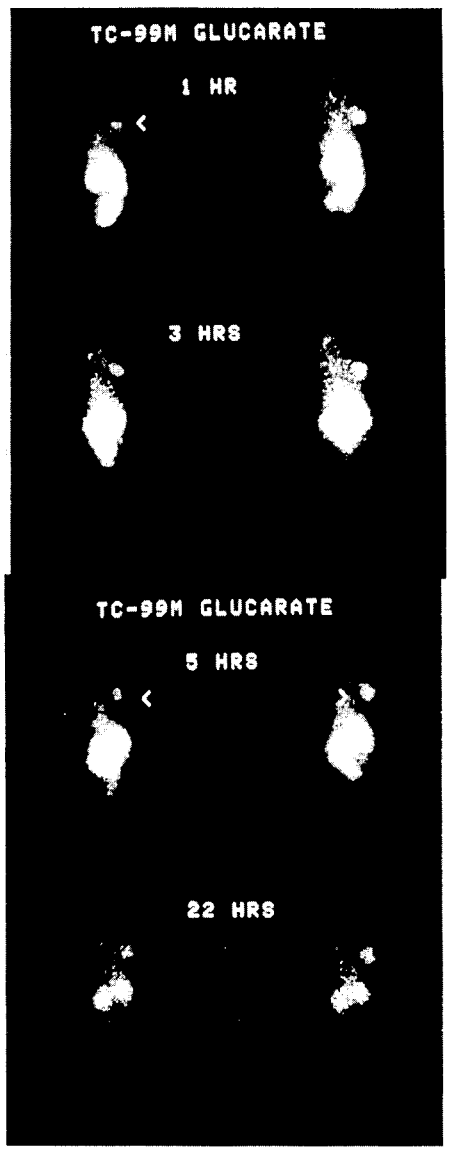
FIG. 2 shows scintigraphic images of breast carcinoma in mice taken at 1 and 3 hours (top) and 5 and 22 hours (bottom) after injection of Tc-99m-glucarate.

The weight of their tumors were 0.187 and 0.237 gm, respectively. Scintigraphic images of breast carcinoma bearing nude mice (n=2) at 1, 3, 5 and 22 hours post administration of Tc-99m-glucarate is shown in FIG. 2. Visualization of the tumor was possible as early as one hour after injection, and minimal blood pool activity was detected. The % ID/gm of the radioactivity at the tumor site was 1.7%, the ratio of tumor to blood, tumor to liver and tumor to muscle were 4.75, 7.1 and 44 respectively at 22 hours.

Equivalents

Those skilled in the art will recognize, or be able to ascertain using no more than routine experimentation, many equivalents to the specific embodiments of the invention described herein. Such equivalents are intended to be encompassed by the following claims.

We claim:

1. A method of obtaining an image of a tumor in a subject, comprising the steps of:
   a. injecting parenterally an effective imaging amount of $^{99m}$Tc-glucarate into the subject;
   b. allowing the $^{99m}$Tc-glucarate to localize at the site of the tumor; and
   c. scanning the subject with a gamma camera to obtain an image of the tumor.

2. A method of claim 1, wherein the tumor is a breast tumor or colorectal tumor.

3. A method of claim 2, wherein $^{99m}$Tc-glucarate is administered intravenously.

* * * * *